United States Patent
Young et al.

[11] Patent Number: 5,989,398
[45] Date of Patent: Nov. 23, 1999

[54] CALORIMETRIC HYDROCARBON GAS SENSOR

[75] Inventors: Daniel A. Young, Gurnee, Ill.; Adam Moya; Chowdary R. Koripella, both of Albuquerque, N. Mex.; Jeff Naber, Dearborn, Mich.; Neil Adams, Novi, Mich.; Craig Markyvech, Romulus, Mich.; Adam Miller, Chicago, Ill.

[73] Assignee: Motorola, Inc., Schaumburg, Ill.

[21] Appl. No.: 08/970,837

[22] Filed: Nov. 14, 1997

[51] Int. Cl.[6] .......................... G01N 27/26; G01N 27/419
[52] U.S. Cl. .......................... 204/424; 204/421; 204/427; 204/408
[58] Field of Search .................... 204/408, 431, 204/432, 430, 421, 422, 423, 424, 425, 426, 427, 428, 429; 422/94, 95, 98

[56] References Cited

U.S. PATENT DOCUMENTS

| | | | |
|---|---|---|---|
| 4,541,988 | 9/1985 | Tozier et al. ................. | 422/94 |
| 4,597,850 | 7/1986 | Takahasi et al. . | |
| 4,614,721 | 9/1986 | Goldberg .................. | 436/147 |
| 4,654,624 | 3/1987 | Hagan et al. .............. | 338/34 |
| 4,905,652 | 3/1990 | Nakajima et al. . | |
| 4,911,892 | 3/1990 | Grace et al. ................ | 422/94 |
| 4,927,517 | 5/1990 | Mizutani et al. . | |
| 5,177,464 | 1/1993 | Hamburg . | |
| 5,250,169 | 10/1993 | Logothetis et al. . | |
| 5,265,417 | 11/1993 | Visser et al. . | |
| 5,444,974 | 8/1995 | Beck et al. . | |
| 5,451,371 | 9/1995 | Zanini-Fisher et al. ................... | 422/51 |
| 5,473,304 | 12/1995 | Friese et al. . | |
| 5,476,001 | 12/1995 | Hoetzel et al. . | |
| 5,494,826 | 2/1996 | Stetter et al. ............... | 436/147 |
| 5,505,073 | 4/1996 | Gerblinger et al. . | |
| 5,505,837 | 4/1996 | Friese et al. . | |
| 5,795,545 | 8/1998 | Koripella et al. . | |

FOREIGN PATENT DOCUMENTS

| | | |
|---|---|---|
| 259175 | 9/1987 | European Pat. Off. . |
| 576932 | 1/1994 | European Pat. Off. . |
| 704697 | 9/1995 | European Pat. Off. . |
| 704698 | 9/1995 | European Pat. Off. . |
| 271379 | 8/1989 | Germany . |
| WO 97/33165 | 11/1996 | WIPO . |

*Primary Examiner*—Robert J. Warden, Sr.
*Assistant Examiner*—Andrew Aldag
*Attorney, Agent, or Firm*—Jasper W. Dockrey

[57] ABSTRACT

A calorimetric hydrocarbon gas sensor (10) includes an electrochemical oxygen pump (18), a sensing element (12), and a multi-layered substrate (26) separating the sensing element (12) from the electrochemical oxygen pump (18). The multi-layered substrate (26) includes a plurality of overlying insulating layers, in which at least one intermediate layer (60) supports a first primary heater (58), and in which another intermediate layer (52) supports a temperature compensation heaters (50a, 50b). The primary heater (58) functions to maintain the calorimetric hydrocarbon gas sensor (10) at a constant, elevated temperature, while the active compensation heater (50a) functions to maintain substantially equal temperatures as determined by the thermometers (46a, 46b) located on an intermediate layer (48) overlying the compensation heaters (50a, 50b). Control circuitry is integrated with power measurement circuitry to measure differences in the heat produced by the compensation heater (50a) and the thermometer (46a) in an active region (100), and the heat produced by the compensation heater (50b) and the thermometer (46b) in a reference region (102).

14 Claims, 5 Drawing Sheets

CALORIMETRIC HYDROCARBON GAS SENSOR

FIELD OF THE INVENTION

This invention relates, in general, to gas component sensors, and more particularly, to calorimetric hydrocarbon gas sensors for the detection of hydrocarbon species in engine exhaust systems.

BACKGROUND OF THE INVENTION

Sensors for the detection of particular compounds present in a high temperature gas stream find numerous applications in many different mechanical systems. For example, detection of certain compounds in a high temperature gas stream is important in industrial emission monitoring for detection of gas pollutants, such as sulfur dioxide ($SO_2$), in residential heating systems for detection of carbon monoxide (CO), and in automobile exhaust systems for various compounds including hydrocarbons.

In automotive applications, gas sensors can be placed at various locations in an exhaust system. Exhaust gas from an internal combustion engine typically contains hydrogen ($H_2$), carbon monoxide (CO), methane ($CH_4$), carbon dioxide ($CO_2$), nitric oxide (NO), water ($H_2O$), and nonmethane hydrocarbons ($C_nH_m$), where n is an integer larger than 1 and m is an integer whose value depends upon the kind of hydrocarbon compound, for example, alkane, alkene, alkyl, or aryl. Important environmental pollution concerns dictate that the emission of hydrocarbons be minimized. To minimize pollutants in the engine exhaust, sensors can be placed before and after the catalytic converter to monitor the performance of the converter. Also, the emission of hydrocarbons can be controlled, in part, by an engine exhaust control system that receives a feedback signal from an exhaust sensor capable of selectively detecting the presence of hydrocarbons in the engine exhaust.

One method for monitoring the performance of a catalytic converter includes the use of oxygen sensors within the exhaust gas system. By measuring the amount of oxygen in the exhaust gas entering and exiting a catalytic converter, an estimate of the amount of oxygen stored in the catalytic converter can be made. Since oxygen storage capacity is necessary for a catalytic converter to oxidize hydrocarbons and reduce nitrogen oxide, an indirect measurement of the pollution control efficiency of the catalytic converter can be made by determining the amount of oxygen stored within the catalytic converter at any given point in time. Accordingly, by estimating the amount of oxygen stored within the catalytic converter, an indirect measurement of the catalytic converter efficiency can be obtained. Although oxygen sensors are relatively simple to manufacture, using oxygen measurements to estimate catalytic converter performance is imprecise.

A sensor that directly estimates the hydrocarbon concentration in an exhaust gas stream can be used to provide a more precise determination of catalytic converter efficiency. For example, several types of sensing elements have been developed for detecting various chemical species within an exhaust gas stream. These sensing elements includes calorimetric sensors having a catalyst coating, semiconductor metal oxide based sensors, and the like. Calorimetric hydrocarbon gas sensors measure the amount of heat released by the catalytic oxidation of hydrocarbons contained within the exhaust gas. To obtain optimum sensitivity for the measurement of hydrocarbon species within an exhaust gas, a calorimetric hydrocarbon gas sensor must be designed to maintain a relatively constant internal temperature. This requirement is especially important given the wide temperature variations encountered in an exhaust gas system, together with the need to internally generate oxygen for catalytic combustion within the sensor.

While providing a measurement of hydrocarbon concentration, a calorimetric hydrocarbon gas sensor must be carefully designed for operation in a high temperature exhaust gas stream. For precise measurement of hydrocarbons in an exhaust gas, small temperature rises, or small quantities of liberated heat, must be detected when the hydrocarbons are oxidized within the sensor. Detection these small variations can be difficult when exhaust gas temperatures are rapidly changing and subjecting the sensor to a variable temperature environment. For example, automotive engine operation is dynamic and the exhaust gas temperature varies from ambient temperature, at engine start-up to more than 1,000° C. during periods of high power operation. Thus, in calorimetric hydrocarbon gas sensor technology for applications to high temperature exhaust gas systems, a major technical challenge involves thermal management within the gas sensor.

In addition to the need to accommodate thermal variations within the exhaust gas, calorimetric sensors require an oxygen source for the catalytic oxidation of the hydrocarbons. Typically, the oxygen supply systems used in calorimetric hydrocarbon gas sensors must operate at elevated temperatures. High temperature operation is necessary to attain the level of efficiency needed to supply sufficient oxygen to the catalyst within the sensor. The necessity of including an oxygen supply system adds additional design constraints for a calorimetric hydrocarbon gas sensor. Thus, improved thermal management is needed within a calorimetric hydrocarbon gas sensor designed for the measurement of hydrocarbons in an exhaust gas stream.

It will be appreciated that for simplicity and clarity of illustration, elements shown in the FIGURES have not necessarily been drawn to scale. For example, the dimensions of some of the elements are exaggerated relative to each other. Further, where considered appropriate, reference numerals have been repeated among the FIGURES to indicate corresponding elements.

DETAILED DESCRIPTION OF PREFERRED EMBODIMENTS

The present invention is for a calorimetric hydrocarbon gas sensor that can be mounted in an automobile exhaust system and used to measure the concentration of non-methane hydrocarbons in the exhaust gas. The gas concentration measurements made by the calorimetric hydrocarbon gas sensor can be converted to electrical signals and relayed to an engine control unit. Electronic circuitry within the engine control unit can analyze the electrical signals from the calorimetric hydrocarbon gas sensor and determine the efficiency of the automobile's catalytic converter at converting hydrocarbons in the exhaust gas to non-polluting gas species. The calorimetric hydrocarbon gas sensor of the invention operates by selectively oxidizing hydrocarbon species within the exhaust gas stream at a catalyst surface located within the gas sensor. In particular, the sensor incorporates thermal measurement devices to measure the amount of heat that is released when hydrocarbon species are oxidized at the catalyst surface. To precisely determine the amount of heat released during hydrocarbon oxidation, the calorimetric hydrocarbon gas sensor of the invention incorporates reference circuitry and temperature compensation circuitry to stabilize the internal temperatures within the sensor. Further, the functional elements of the sensor are arranged in a spaced relationship to one another, such that internal temperature uniformity is optimally maintained.

Figure 1:
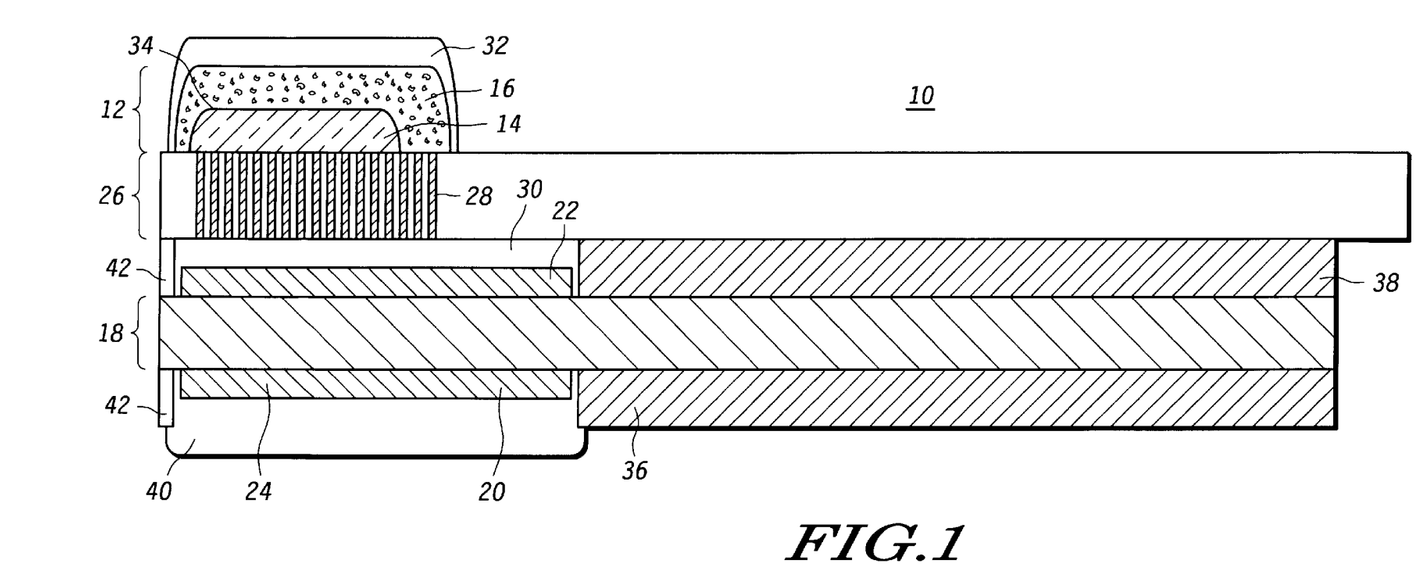
FIG. 1 illustrates, in cross-section, a calorimetric hydrocarbon gas sensor arranged in accordance with one embodiment of the invention.

FIG. 1 illustrates, in cross-section, a calorimetric hydrocarbon gas sensor 10 arranged in accordance with one embodiment of the invention. A sensing element 12 includes a catalyst 14 and an interface region 16. An electrochemical oxygen pump is arranged in spaced relationship with sensing element 12. Electrochemical oxygen pump 18 includes an outer electrode 20 and an inner electrode 22. The electrodes are separated by an electrolyte layer 24. Sensing element 12 is separated from electrochemical oxygen pump 18 by a multi-layer substrate 26. As will subsequently be described, substrate 26 includes a plurality of overlying insulative layers on which electrical circuitry and resistive heating elements are arranged. Additionally, substrate 26 includes a plurality of vias 28. Vias 28 provide communication between interface region 16 and an oxygen storage region 30. As will subsequently be described in greater detail, electrochemical oxygen pump 18, substrate 26, and sensing element 12 are vertically aligned in a stacked relationship to enable substrate 26 to regulate the temperature of both sensing element 12 and electrochemical oxygen pump 18.

A diffusion barrier 32 overlies interface region 16. Diffusion barrier 32 limits the rate at which hydrocarbons diffuse to interface region 16. Once in interface 16, the hydrocarbon gas species diffuse through interface region 16 and are subsequently oxidized at active surface 34 of catalyst 14. Oxygen is present in interface region 16 in sufficient quantities to oxidize all of the hydrocarbon species diffusing through diffusion barrier 32. By controlling the rate of diffusion of hydrocarbon species arriving at active surface 34, the rate at which energy is released by the oxidation reaction can be directly correlated with the concentration of hydrocarbons in the exhaust gas.

Those skilled in the art will recognize that the concentration of hydrocarbons at active surface 34 is not equal to the concentration of hydrocarbons in the exhaust gas at some distance from active surface 34. The diffusive flux of hydrocarbons from the exhaust gas to active surface 34 is a function of the difference in the concentration of hydrocarbons at active surface 34 and the concentration of hydrocarbons elsewhere in the exhaust gas. In a preferred embodiment, the concentration of hydrocarbons at active surface 34 is substantially zero. Diffusion barrier 32 limits the diffusive flux of hydrocarbon species to active surface 34, such that substantially all of the hydrocarbons are oxidized upon arrival at active surface 34. Accordingly, the diffusive flux of hydrocarbons across diffusion barrier 32 will be proportional to the hydrocarbon concentration in the exhaust gas. Moreover, the diffusion of hydrocarbon species through diffusion barrier 32 is the rate determining step governing the transport of hydrocarbon species from the exhaust gas to active surface 34.

The important aspects of the invention described above permit calorimetric hydrocarbon gas sensor 10 to accurately determine the hydrocarbon concentration in the exhaust gas by means of measuring the amount of heat released by exothermic catalytic reactions. Since all of the hydrocarbons must be completely oxidized to maintain a near-zero hydrocarbon concentration at active surface 34, the heat released by the exothermic oxidation reaction will also be proportional to the hydrocarbon concentration in the exhaust gas. Furthermore, with diffusive transport through diffusion barrier 34 largely determining the flux of hydrocarbon species arriving at active surface 34, this flux is less sensitive to other elements of the hydrocarbon transport process, such as diffusion through the exhaust gas or convective transport by the exhaust gas. As a result, the proportionality constant between the heat released by exothermic oxidation and the hydrocarbon concentration in the exhaust gas is largely unaltered by variations in other transport processes.

In addition to limiting the hydrocarbon diffusive flux to active surface 34, diffusion barrier 32 also functions to protect catalyst 14 from scouring by particles entrained in the flowing exhaust gas. Further, by reducing heat exchange between the sensor and the environment, diffusion barrier 32 serves to limit temperature fluctuations in the heat measuring devices located in heating element 26. In the absence of diffusion barrier 32, temperature fluctuations in the exhaust gas could be transmitted to the temperature measuring devices without attenuation. Unattenuated temperature fluctuations can cause signal noise in the sensor output. The ability of diffusion barrier 32 to maintain a stable diffusion rate is enhanced by thermally coupling diffusion barrier 32 to heating element 26, and, indirectly, to catalyst 14. Preferably, diffusion barrier 32 has a low porosity and is constructed from low-porosity alumina. Low-porosity alumina is made by mixing relatively small quantities of large organic additives with the alumina base prior to firing the material. Alternatively, a low-porosity material, such as spinel, cordierite, mullite, steatite, stabilized zirconia, or another porous ceramic material can be used. Preferably, interface region 16 is constructed from a high-porosity material, such as high-porosity alumina. High-porosity alumina is made by mixing a relatively large quantities of organic additives with the alumina base. Alternatively, a high-porosity material, such as spinel, cordierite, mullite, steatite, stabilized zirconia, or other porous ceramic material can be used. In yet another alternative, interface region 16 can be a gas cavity within calorimetric hydrocarbon gas sensor 10.

Electrochemical oxygen pump 18 is separated from substrate 26 by first and second ceramic layers 36 and 38. Preferably, electrolyte 24 is yttrium stabilized zirconia, and outer and inner electrodes 20 and 22 are constructed of porous platinum metal. Placing a voltage across electrodes 20 and 22 generates oxygen by breaking down water and carbon dioxide in the exhaust gas at outer electrode 20 and conducting oxygen ions across electrolyte 24 to inner electrode 22. A porous protective layer 40 overlies outer electrode 20 and extends from first ceramic layer 36 to a sensor end wall 42. Porous protective layer 40 functions to protect outer electrode 20 from scouring by the exhaust gas, while permitting water and carbon dioxide to diffuse to outer electrode 20. Preferably, porous protective layer 40 is constructed from a high-porosity material, such as high-porosity alumina. Alternatively, a material, such as spinel, cordierite, mullite, steatite, stabilized zirconia, or another porous ceramic material can be used.

Oxygen that desorbs from inner electrode 22 is contained within oxygen storage region 30. Oxygen storage region 30 extends from second ceramic layer 38 to end wall 42. Oxygen then diffuses through vias 28 to interface region 16. In addition to providing an oxygen source for catalytic oxidation of hydrocarbons at active surface 34, oxygen pump 18 can be operated in reverse to remove oxygen from interface region 16 and oxygen storage region 30. Furthermore, oxygen pump 18 can be used to break down water and carbon dioxide at inner electrode 22. Hydrogen and carbon monoxide, produced in this process, are desorbed from inner electrode 22 into oxygen storage region 30, then diffuse through vias 28 into interface region 16. However, oxygen ions are conducted across electrolyte 24 to outer electrode 20 and desorbed into the exhaust gas. Also, oxygen entering interface region 16 through diffusion barrier 32 is preferentially consumed by catalyzed combustion with hydrogen and carbon monoxide, limiting hydrocarbon combustion with oxygen from that source. By removing the available oxygen, the oxidized combustion of hydrocarbons within calorimetric hydrocarbon gas sensor 10 can be effectively terminated. By terminating the catalytic oxidation of hydrocarbons at active surface 34, calorimetric hydrocarbon gas sensor 10 can be calibrated after installation into an automotive exhaust gas system.

Figure 2:
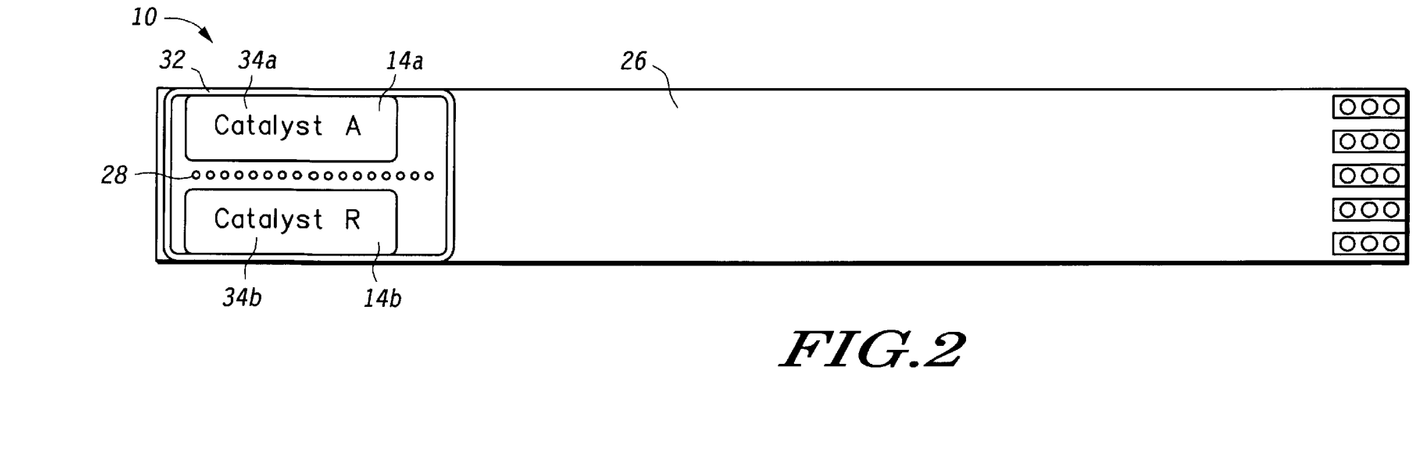
FIG. 2 illustrates a top view of the calorimetric hydrocarbon gas sensor shown in FIG. 1.

FIG. 2 shows a top view of calorimetric hydrocarbon gas sensor 10 illustrating the arrangement of catalyst 34 and vias 28. Catalyst 34 is partitioned into an active region 14a and a reference region 14b. Active region 14b includes a catalyst composition specifically formulated to catalyze the oxidation of hydrocarbons at active surface 34a. However, the catalyst in reference region 14b lacks the specific chemical formulation necessary to catalyze the oxidation of hydrocarbons at active surface 34b. Accordingly, the exothermic reaction heat measured by temperature sensing circuitry for reactions taking place at active surface 34b can be compared with the exothermic reaction heat measured at active surface 34a. The difference in the amount of heat produced between active region 14a and reference region 14b is attributed to the oxidation of hydrocarbon species within the exhaust gas.

Figure 3:
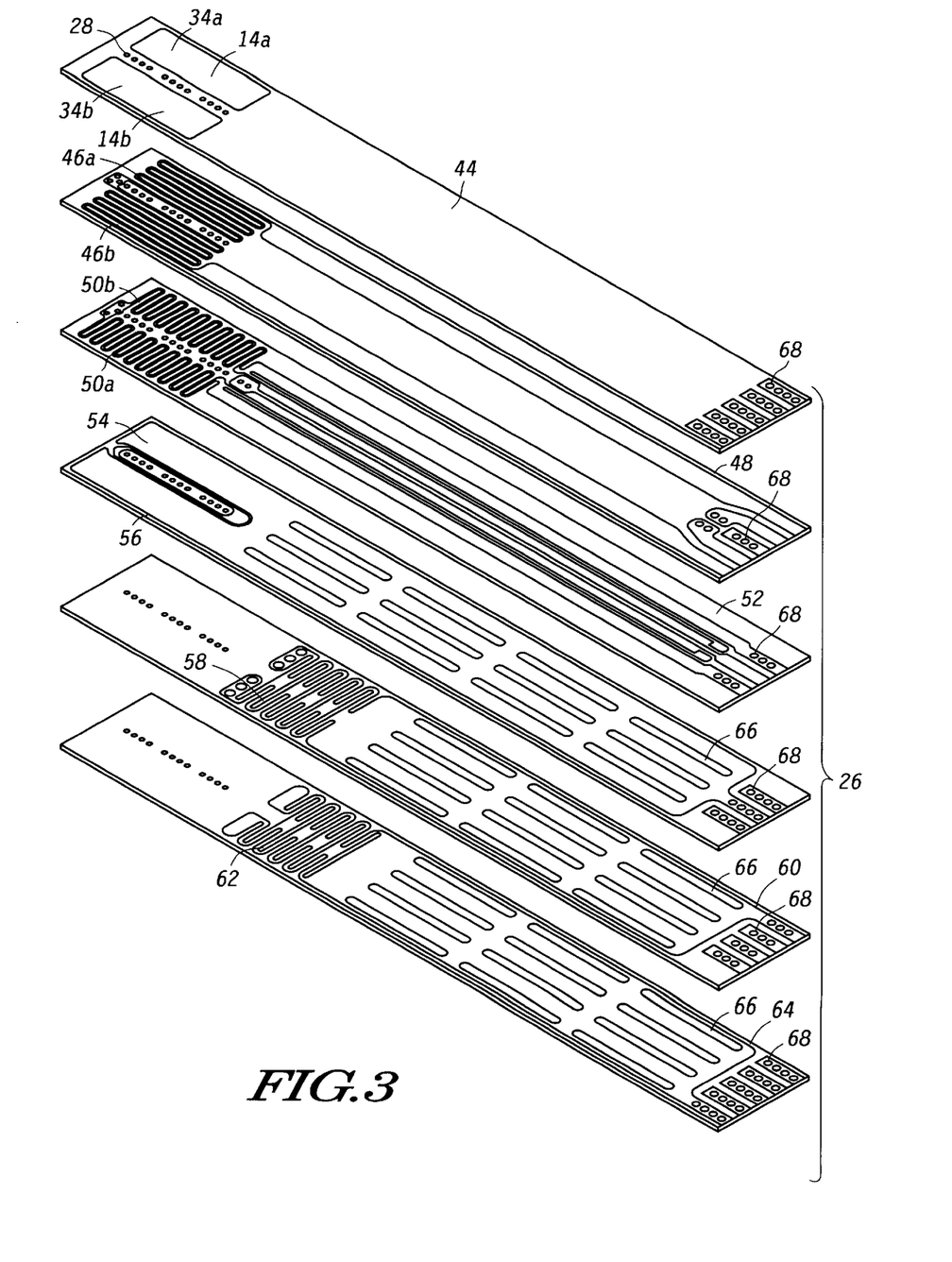
FIG. 3 is an exploded perspective view of a multi-layered substrate arranged in accordance with the invention.

FIG. 3 is an exploded perspective view of substrate 26 showing a plurality of overlying insulative layers that are laminated together to form substrate 26. In a preferred embodiment, each of the plurality of overlying insulative layers are ceramic layers laminated together to form a multi-layered ceramic substrate. With the exception of top layer 44, each ceramic layer supports screen-printed metallization defined in different patterns to form the various functional elements necessary to measure and control temperature within calorimetric hydrocarbon gas sensor 10. Thermometers 46a and 46b overlie intermediate layer 48. Thermometers 46a and 46b reside directly below active regions 14a and 14b, respectively, and function to measure the average and the differential temperature of the active and reference catalyst disposed on the surface of top layer 44. Compensation heaters 50a and 50b are disposed on the surface of intermediate layer 52 and reside directly below compensation heaters 46a and 46b, respectively. Metallization 54 overlies intermediate layer 56 and provides an electrical ground plane to electrically isolate compensation heaters 50a and 50b from first primary heater 58 located on intermediate layer 60. A second primary heater 62 resides on bottom layer 64 and is positioned generally below first primary heater 58.

In addition to the various ceramic layers shown in FIG. 3, substrate 26 can include additional layers to promote the mechanical strength and optimize the thermal conductance of substrate 26. Importantly, the metallization overlying intermediate layers 56 and 60, and bottom layer 64 includes a plurality of slots 66 that function to promote adhesive bonding within substrate 26.

In general, substrate 26 is fabricated by first forming electrical vias 68 in each layer of green tape and filling the vias with metal, followed by screen-printing metal onto individual layers of ceramic green tape. Electrical vias 68 provide a means to establish electrical communication between the various layers of substrate 26. Next, the layers are pressed together and fired at high temperature, then the catalyst is screen printed onto the surface of substrate 26 and fired at high temperature.

In operation, voltage is applied to primary heaters 58 and 62 to bring calorimetric hydrocarbon gas sensor 10 to a predetermined stable temperature, as measured by thermometer 46b. As exothermic oxidation reactions occur on active surfaces 34a and 34b, different temperature rises are detected by thermometers 46a and 46b. To compensate for the temperature rises detected by thermometers 46a and 46b, the applied voltage or current flowing in compensation heater 50a is used to adjust the electrical power dissipated in compensation heater 50a until the temperature of thermometers 46a and 46b becomes equal. Accordingly, the power adjustment to compensation heater 50a that is necessary to return thermometers 46a and 46b to equal temperatures, is proportional to the difference in the exothermic oxidation heat generated by the catalytic reactions.

In practice, the power supplied to compensation heaters 50a and 50b is controlled by an external electrical circuit (not shown). The voltage across each compensation heater is measured by an external, high-impedance electrical circuit (not shown) that does not draw appreciable current. Use of the high impedance device permits the width of the metal traces connected to compensation heaters 50a and 50b to be very narrow without inducing unacceptable voltage drops in the heater voltage measurements. The metal traces carrying current to compensation heaters 50a and 50b have sufficient width to ensure that the heat dissipated in the traces is limited, and does not degrade the power difference measurement used to determine the difference in the exothermic oxidation heat generated by the catalytic reactions.

In accordance with the invention, the primary heaters and compensation heater are arranged within substrate 26 and used to fix the temperature of thermometers 46a and 46b. The arrangement provides a fixed relationship between the power dissipated in the compensation heaters 50a and 50b and the heat generated by exothermic oxidation reactions occurring at catalysts 14a and 14b. Compensation of the heat generated by oxidation reactions occurring at catalyst 14a and 14b using compensation heaters 50a and 50b reduces the thermal dissipation in intermediate layers 48, 52, 56, 60 and bottom layer 64. The precise thermal management obtained within substrate 26, provides for a rapid response to temperature changes occurring at top layer 44.

Thermal management is an important aspect of the invention because heat conduction within substrate 26 can introduce error in the measurement of heat generated by exothermic oxidation reactions. Thus, in accordance with the invention, the temperature of top layer 44 varies in proportion to heating from oxidation reactions and the thermal response time is determined primarily by the time required for heat to diffuse through top layer 44 to thermometers 46a and 46b. By controlling the temperature variation of all portions of substrate 26, the power dissipated in the compensation heaters 50a and 50b is proportional to the heat generated by exothermic oxidation reactions occurring at catalysts 14a and 14b. A calibration method and electrical control arrangement to maintain temperature control within the hydrocarbon gas sensor of the invention will subsequently be described.

Figure 4:
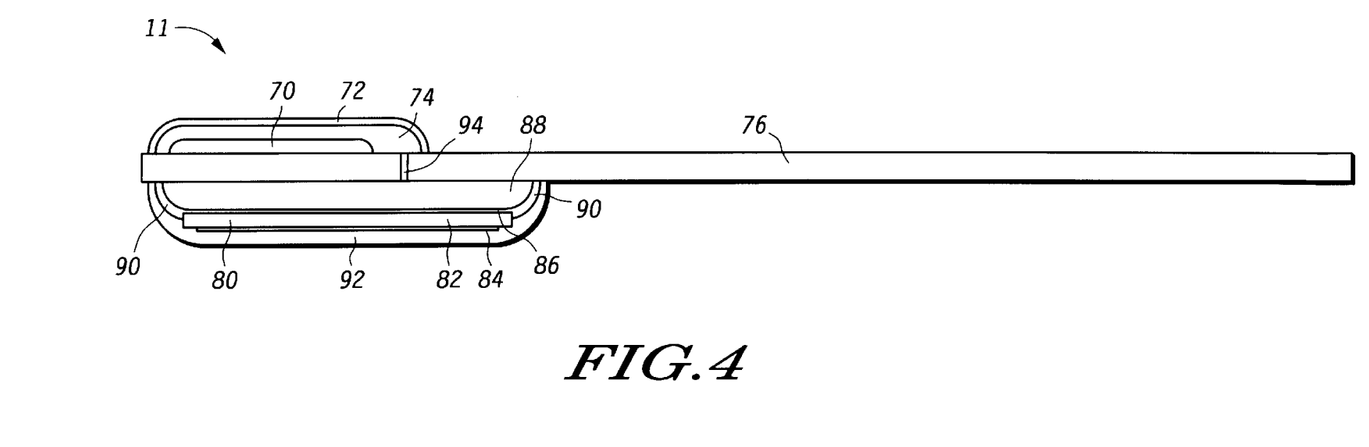
FIG. 4 illustrates, in cross-section, a calorimetric hydrocarbon gas sensor arranged in accordance with an alternative embodiment of the invention.

An alternative embodiment of the invention is illustrated, in cross-section, in FIG. 4. The alternative embodiment includes a catalyst layer 70 encased within a low-porosity diffusion barrier 72 and separated therefrom by a high-porosity lateral transport layer 74. Catalyst 70 overlies a multi-layer substrate 76. An oxygen pump 80 resides below substrate 76 and generally opposite from catalyst 70. Oxygen pump 80 includes a zirconia electrolyte layer 82 and porous platinum electrodes 84 and 86. Oxygen pump 80 is separated from substrate 76 by a second high-porosity lateral transport layer 88. Areas of high-porosity lateral transport layer 88 not in contact with platinum electrode 86 are covered by an impermeable layer 90. Oxygen pump 80 and high-porosity lateral transport 88 are encased within a porous protective layer 92. In comparison with the previous embodiment, the oxygen pump of the embodiment illustrated in FIG. 4 includes a less extensive zirconia electrolyte layer. By restricting the lateral extent of the oxygen pump, more precise thermal management is possible within the calorimetric hydrocarbon gas sensor.

Figure 5:
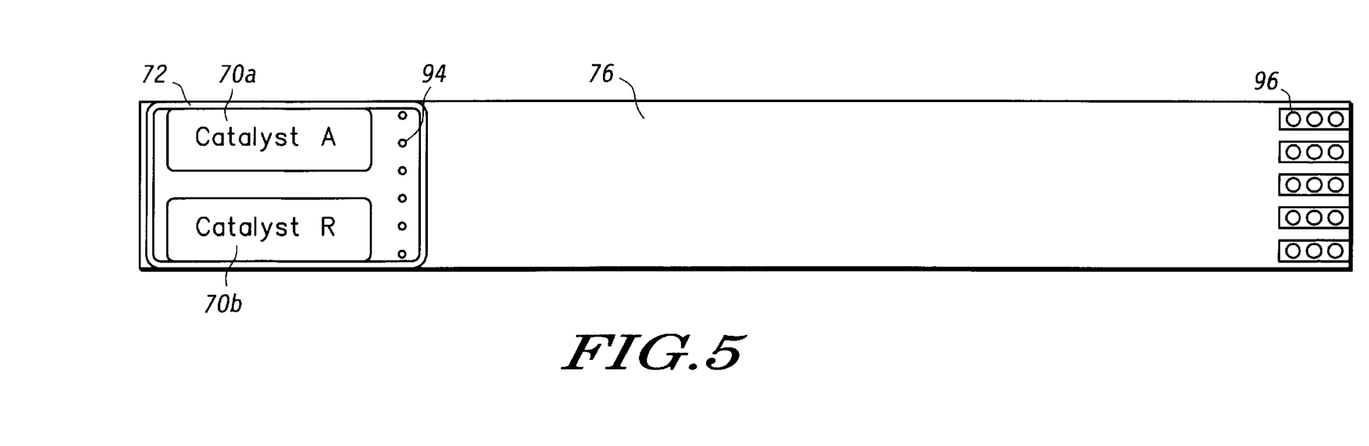
FIG. 5 illustrates a top view of the calorimetric hydrocarbon gas sensor shown in FIG. 4.

A top view of calorimetric hydrocarbon gas sensor 11 is shown in FIG. 5. A plurality of vias 94 extend through substrate 76 and connect high-porosity lateral transport layers 88 and 74. In a manner analogous to the previous embodiment, vias 94 provide a diffusion pathway for oxygen produced by oxygen pump 80 to diffuse through substrate 76. In contrast with the previous embodiment, vias 94 are aligned adjacent to low-porosity diffusion barrier 72. By comparing FIGS. 2 and 5 it becomes apparent that the invention contemplates the formation of vias in the substrate in a variety of geometric configurations. Additionally, it is contemplated that the vias be open, or alternatively that they be filled with a porous material.

Catalytic oxidation of the combustible components of the exhaust gas, including hydrocarbons, is carried out in active region 70a, while selective oxidation of the combustible components of the exhaust gas, excluding hydrocarbons, occurs at reference region 70b. A plurality of electrical vias 96 provide electrical connection to the various layers within substrate 76.

Figure 6:
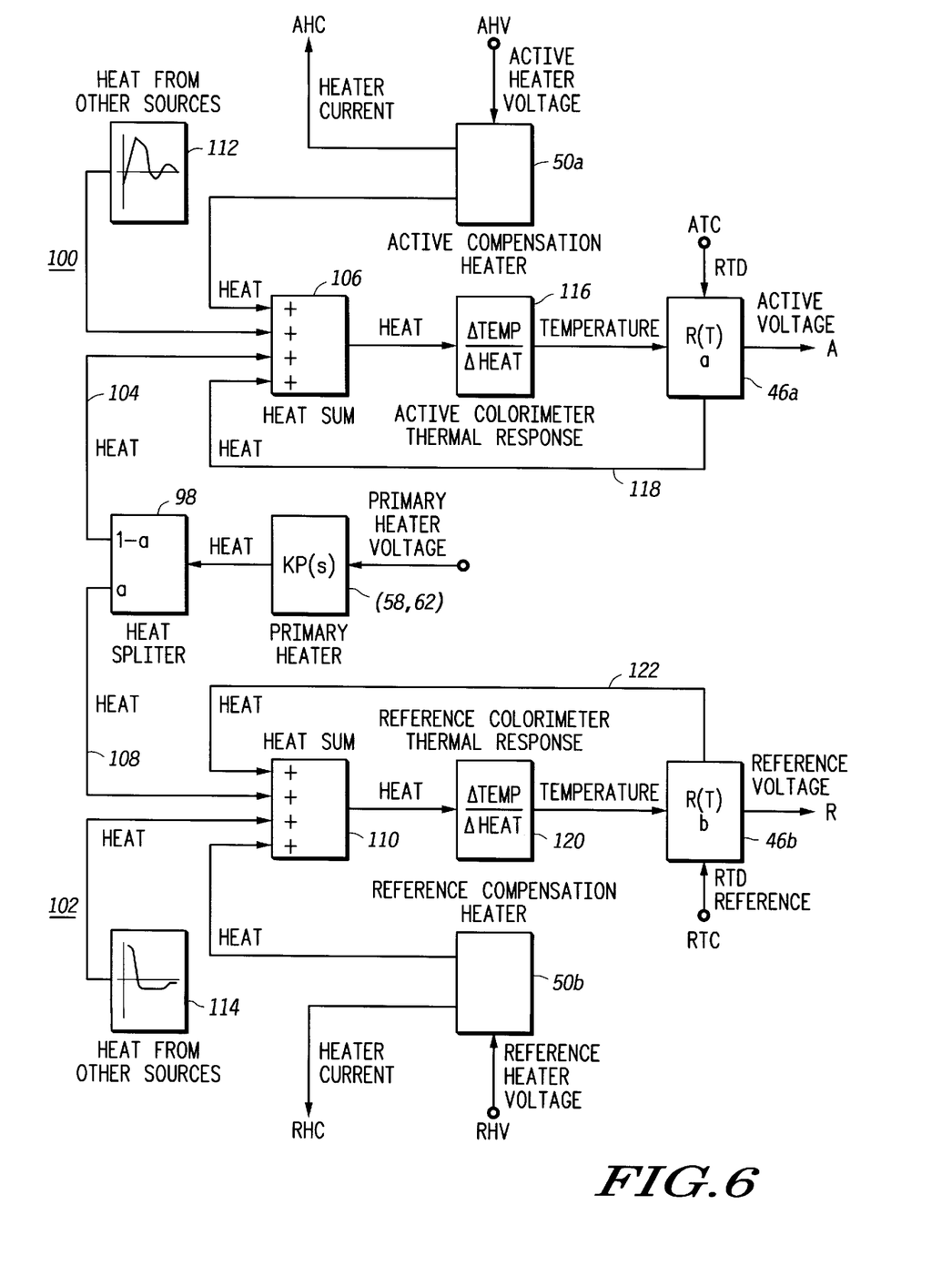
FIG. 6 is a schematic diagram of the thermal coupling and electrical interfaces for the calorimetric hydrocarbon gas sensor shown in FIGS. 1 and 4.

FIG. 6 is a schematic diagram showing the thermal coupling and electrical interfaces for the hydrocarbon gas sensor of the invention. The schematic diagram represents, in part, a conceptualization of the flow of heat within the regions of calorimetric gas sensor 10 in conjunction with the sensor components previously described. The schematic diagram also illustrates electrical interfaces necessary to provide operating power to and receive information from the various components within substrate 26.

Referring to FIG. 6, a control voltage is input into first primary heater 58 or second primary heater 62, or both. The heat generated by the input voltage is divided into two legs by a heat splitter 98. Heat splitter 98 divides the heat generated by the primary heaters into a active region 100 and into a reference region 102 of calorimetric gas sensor 10.

Recalling the components illustrated in FIG. 2, active region 100 is generally associated with catalyst 14a, thermometer 46a, and compensation heater 50a, while reference region 102 is generally associated with catalyst 14b, thermometer 46b, and compensation heater 50b.

A first leg 104 represents heat transfer from the primary heater to active region 100, and a second leg 108 represents heat transfer from the primary heater to reference region 102. In addition to receiving heat from the primary heater, active region 100 and reference region 102 receive heat from external sources 112 and 114, respectively. The summation of the heat inputs to active region 100 and reference region 102 is represented by heat sums 106 and 110, respectively. Ideally, external sources 112 and 114 correspond to catalyst surfaces 34a and 34b, respectively, and associated thermal loading in the ceramic materials and metal wiring. However, because calorimetric gas sensor 10 operates in a high temperature gas stream, external sources 112 and 114 also include thermal loading from heat transfer between the high temperature exhaust gas and the sensor components.

In addition to receiving heat from the primary heater and the external sources, active region 100 also receives heat from compensation heaters 50a and heat dissipation 118 in thermometer 46a arising from the operating current applied to thermometer 46a. Summation of heat from these sources is represented by heat sum 106. Similarly, in addition to receiving heat from the primary heater and external sources, reference region 102 receives heat from compensation heater 50b and heat dissipation 122 in thermometer 46b arising from the operating current applied to thermometer 46b. Summation of heat from these sources is represented by heat sum 110. The net sum of all of the heat received by active region 100, as represented by heat sum 106, results in a temperature rise as schematically shown by operation 116. This temperature is then measured by thermometer 46a. A corresponding heat transfer occurs in reference region 102. Operation 120 converts heat from heat sum 110 into a temperature rise measured by thermometer 46b.

Figure 7:
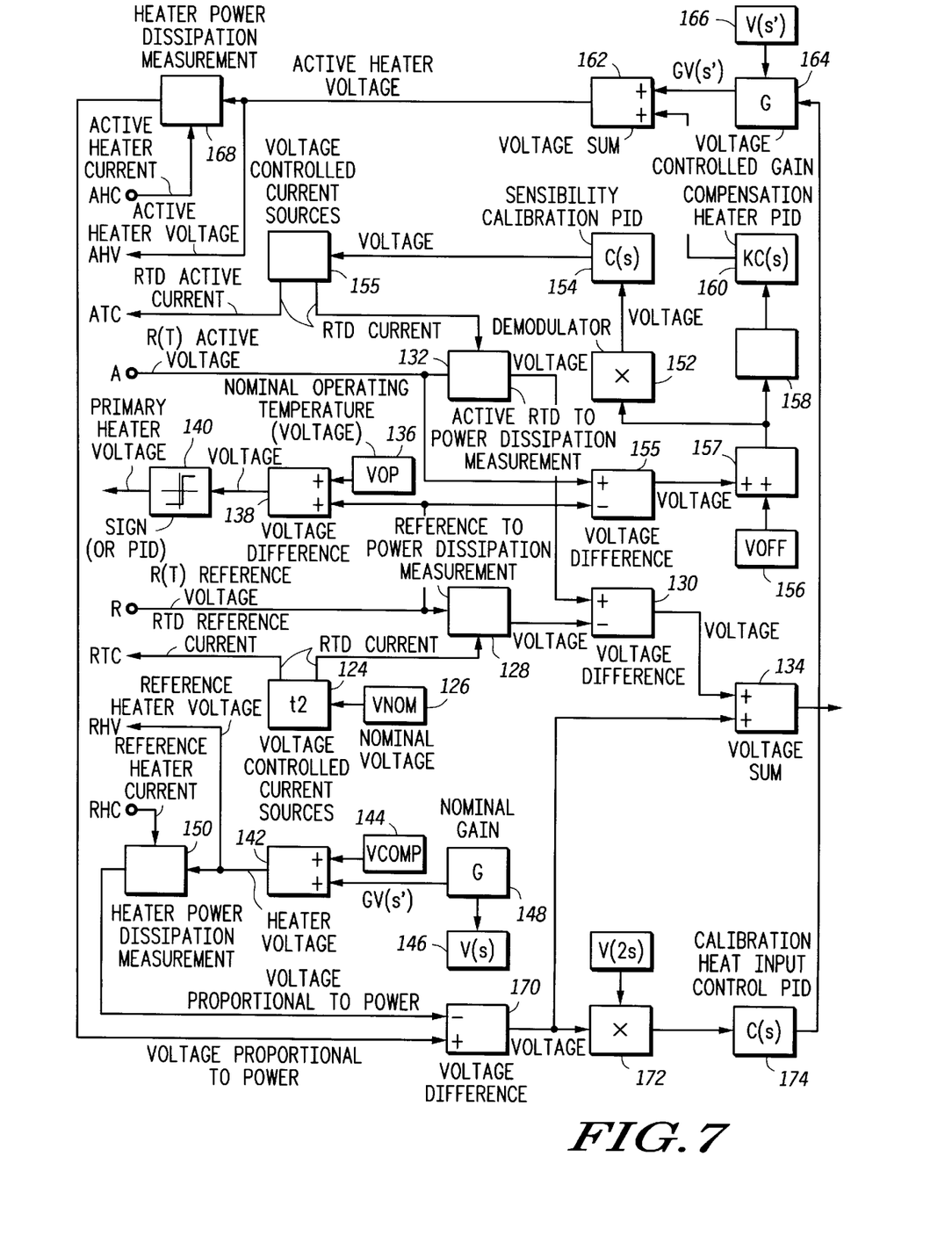
FIG. 7 is a schematic circuit diagram of one embodiment of a calibration and control circuitry for the calorimetric hydrocarbon gas sensor.

Thermometer 46b outputs a reference voltage R to the calibration and control circuitry illustrated in FIG. 7. Correspondingly, thermometer 46a outputs voltage A to the calibration and control circuitry. Further, compensation heaters 50a and 50b output heater current signals AHC and RHC, respectively, to the calibration and control circuitry. In turn, the calibration and control circuitry provides voltage to primary heaters 58 and 62, voltage AHV to compensation heater 50a, voltage RHV to compensation heater 50b, operating current ATC to thermometer 46a, and operating current RTC to thermometer 46b.

In the present invention, the control circuitry is integrated with power measurement circuitry to measure differences in the heat produced by compensation heater 50a and thermometer 46a in active region 100, and by compensation heater 50b and thermometer 46b in reference region 102. The active and reference regions will remain at constant, although not necessarily equal temperatures, if an only if there is no net heat input into either region. For this to be true, the heat input to active region 100 from primary heaters 58 and 62, compensation heaters 50b, and from thermometer 46a must be equal and opposite to the heat from other sources 112. Other sources 112 includes the heat generated by oxidation reactions on catalyst 34a. Similarly, the heat input to active region 110 from primary heaters 58 and 62, compensation heater 50b, and from thermometer 46b must be equal and opposite to the heat from other sources 114, including heat generated by oxidation reactions on catalyst 34b.

The control circuitry shown in FIG. 7 maintains active region 100 and reference 102 at constant, elevated, and equal temperatures. Maintaining the regions at a constant, elevated temperature, as measured by thermometer 46b, is accomplished by adjusting the rate at which heat is supplied to reference region 102 by primary heaters 58 and 62. The difference between the actual voltage across thermometer 46b and a nominal operating voltage, equal to the voltage across thermometer 46b at the desired elevated temperature produced by voltage source 136, is determined by a voltage comparator 138. Voltage comparator 138 outputs a voltage signal to primary heater controller 140, which relays a heater voltage to the primary heaters 58 and 62. Controller 140 computes the derivative with respect to time and the integral over time of the voltage signal from voltage comparator 138 and produces an output voltage equal to the weighted sum of the input voltage signal, the derivative of input voltage, and the integral of the input voltage signal over time. Since the primary heaters nominally supply heat to active region 100 at the same rate as reference region 102, the temperature increases produced in the two regions by the primary heater are nearly equal.

Compensation heaters 50a and 50b are employed to maintain active region 100 and reference region 102 at equal temperatures. A nominal quantity of heat, larger than the differential heat arising from chemical reactions occurring at catalysts 34a and 34b, is supplied to compensation heaters 50a and 50b. Changes in the temperature difference between active region 100 and reference region 102 are monitored and the quantity of heat supplied by compensation heaters 50a is adjusted to maintain a constant temperature difference. The changes in the heat supplied by compensation heaters 50a and 50b are equal and opposite to changes in the differential heat supplied from catalysts 34a and 34b. In this manner, control and measurement circuitry determines the precise amount of heat being generated by the oxidation of hydrocarbons in calorimetric gas sensor 10.

The resistance of thermometers 46a and 46b is measured by establishing a nominal electrical current in each thermometer and measuring the voltage across each thermometer. In the case of thermometer 46b in reference region 102, a reference current RTC is supplied to thermometer 46b by a current source 124 controlled by a nominal voltage source 126, as shown in FIG. 7. A power measurement circuit 128 receives the current from source 126 and a voltage signal R from thermometer 46b, and outputs a voltage signal proportional to the electrical power dissipated in thermometer 46b to a voltage comparator 130. A similar measurement is performed from thermometer 46a by a power measurement circuit 132. Power measurement circuit 132 receives current from source 156 and a voltage signal A from thermometer 46a, and outputs a voltage signal to voltage comparator 130. Voltage comparator 130 compares the voltage signals from circuits 128 and 132 and outputs a voltage signal proportional to the difference in the electrical power dissipated in the thermometers to voltage summation circuit 134.

To insure a certain minimum amount of heat dissipation in compensation heater 50b, a nominal, fixed compensation heater voltage 144 is supplied to voltage summation circuit 142. A fixed, sinusoidal voltage component of frequency s' is also received by summation circuit 142 from voltage oscillator 146 after application of a nominal, fixed gain by gain circuit 148. The magnitude of the gain applied by gain circuit 148 is chosen to provide a quantity of power to compensation heater 50b at twice the frequency of the sinusoidal voltage signal. The magnitude is such that a time-varying temperature change is readily detectable by thermometer 46b. Power measurement circuit 150 uses the voltage supplied to compensation heater 50b RHV and the current measured in compensation heater 50b RHC to compute the power dissipated by heater 50b. Thus, the power dissipation computed by circuit 150 includes a time-varying component at frequency 2s'. As will subsequently be described, the presence of the time-varying voltage component in the reference region 102 permits continuous calibration of calorimetric gas sensor 10.

Compensation heater 50b, which is used to maintain active region 100 and reference region 102 at equal temperatures, is controlled using the difference between the output voltages of thermometers 46a and 46b computed by voltage comparator 155. An static offset voltage is added to the difference by voltage source 156 to compensate for static offset differences in the response, which can be measured in the absence of the catalytic oxidation of hydrocarbons. The high frequency components of the voltage signal are removed by a low pass filter 158. A controller 160 receives the voltage signal and computes the derivative with respect to time and the integral of the voltage signal over time. Controller 160 outputs a weighted sum of the input signal, the derivative, and the integral to a voltage summation circuit 162. Gain circuit 164 applies a voltage gain to a signal received from a voltage oscillator 166 and outputs a sinusoidal voltage GV(s') to summation circuit 162. The output voltage AHV of summation circuit 162 is supplied to compensation heater 50a.

The current supplied to compensation heater 50a and the active heater voltage supplied to compensation heater 50a are received by a power measurement circuit 168. The power dissipated by compensation heater 50a is computed by power measurement circuit 168 and an output signal is sent to voltage difference circuit 170. Difference circuit 170 receives a power signal for compensation heater 50b and subtracts that signal from the power signal for compensation heater 50a output by measurement circuit 168. The output of voltage difference circuit 170, which is proportional to the difference in the power dissipated in compensation heaters 50a and 50b, is supplied to summation circuit 134, along with the thermometer power difference signal.

The output of voltage summation circuit 134 is proportional to the difference in the net power supplied to active region 100 and reference region 102. It is important to note that the output of voltage summation circuit 134 is the main output signal from calorimetric hydrocarbon gas sensor 10. This output can be routed to a monitoring device or other electronic apparatus designed to receive and interpret signals from gas sensor 10.

A calibration method will now be described. To provide the most accurate measurements, equal heat inputs to the active region heat sum 106 and reference region heat sum 110 must result in the generation of equal signals by thermometers 46a and 46b. Since the output of thermometer 46a is proportional to the applied current ATC, this current can be adjusted to equalize the signals generated by thermometers 46a and 46b in response to equal heat inputs. It is possible to intermittently interrupt operation of the sensor, establish equal heat inputs, and adjust the current ATC to provide equalized response. Alternatively, this response equalization procedure could be performed when the sensor is not in use. Continuous adjustment of the response equalization can be performed by supplying equal quantities of sinusoidally varying power at frequency 2s' to compensation heaters 50a and 50b and subsequently adjusting the current ATC applied to thermometer 46a to equalize the voltage signals at frequency 2s' from thermometers 46a and 46b.

Continuous adjustment of the response equalization is implemented in the control circuitry.

To establish equal quantities of sinusoidally varying power at frequency 2s' to compensation heaters 50a and 50b, the amplitude of the component at frequency 2s' contained in the compensation heater power difference signal output from difference circuit 170 is measured by demodulator 172. Demodulator 172 outputs the measured amplitude to a calibration controller 174. Calibration controller 174 computes the derivative and the integral over time of the measured amplitude and outputs a control signal to gain circuit 164. The control signal is equal to the weighted sum of the measured amplitude, the derivative, and the integral of the measured amplitude. Gain circuit 164 uses the weighted sum to set the applied gain level and produce output signal GV(s'). The summation circuit 162 adds the value of GV(s') to the output from controller 160 to produce the active heater voltage signal AHV applied to compensation heater 50a. Thus, equal quantities of sinusoidally varying power at frequency 2s' are supplied to compensation heaters 50a and 50b.

The difference in the output signal at frequency 2s' from thermometers 46a and 46b is measured by demodulator 152 and supplied to controller 154. Sensitivity calibration controller 154 computes the derivative and the integral over time of the signal and outputs a control signal to current source 156, which supplies current ATC to thermometer 46a. The control signal is equal to the weighted sum of the measured amplitude, the derivative, and the integral of the measured amplitude.

The control circuitry illustrated in FIGS. 6 and 7 can be grouped according to the functions performed by related circuit elements. A reference power equalization control circuit establishes equal quantities of sinusoidally varying power at frequency 2s' in the compensation heaters. A response equalization circuit establishes equal signals from the thermometers at frequency 2s', in response to the equal quantities of sinusoidally varying power at frequency 2s' in the compensation heaters. A primary heater control circuit maintains reference thermometer 46b at constant temperature. A compensation heater control circuit maintains a constant temperature difference between thermometers 46a and 46b. A power difference measurement circuit measures the difference in the heat released by catalyzed oxidation in regions 100 and 102. The output of the power difference measurement circuit is the main output signal of the hydrocarbon sensor.

The major circuits illustrated in FIGS. 6 and 7 can be identified as follows:

the reference power equalization control circuit includes, compensation heaters 50a and 50b, heater power measurement circuits 150 and 168, voltage comparator 170, demodulator 172, voltage oscillators 166 and 167, calibration controller 174 and gain circuit 164:

the response equalization circuit includes thermometers 46a and 46b, current sources 156 and 124, voltage difference circuit 155, demodulator 152, voltage oscillator 153, and calibration controller 154:

the primary heater control circuit includes primary heaters 58 and 62, thermometer 46b, voltage comparator 138, voltage source 136 and primary heater controller 140:

the compensation heater control circuit includes compensation heaters 50a and 50b, thermometers 46a and 46b, voltage difference circuit 155, voltage sources 144 and 156, low pass filter 158 and controller 160:

the power difference measurement circuit includes power measurement circuits 128, 132, 150 and 168, and voltage comparators 130, 134 and 170.

In an alternative embodiment of the control and measurement circuitry, the resistance of compensation heaters 50a and 50b can be used to provide the required temperature measurement, eliminating the need for thermometers 46a and 46b. The resistance temperature measurement is performed by measuring the ratio of the voltage applied to the heater divided by the current flowing in the heater. Similar to the technique described above, the voltages applied to each heater are adjusted to provide a difference in the power dissipated in each heater that will maintain the two heaters at a constant temperature difference. However, the relative thermal response depends on the values of the currents flowing in the two heaters. Since these currents vary as the heater voltages are adjusted to maintain the required difference in power dissipation, they cannot be independently adjusted to equalize the thermal response. Therefore, it is necessary to make response equalization adjustments in the control and measurement circuitry. In addition, the sinusoidally varying powers used in the response equalization process cannot be both produced and measured by the compensation heaters. The sinusoidally varying powers used in the response equalization process could be produced in the primary heaters. In this alternative embodiment, the sensing element is simplified by eliminating the thermometers but more elaborate electronic control and measurement circuitry is required.

Thus it is apparent that there has been provided, in accordance with the invention, a calorimetric hydrocarbon gas sensor that fully meets the advantages set forth above. Although the invention has been described and illustrated with reference to specific illustrative embodiments thereof, it is not intended that the invention be limited to those illustrative embodiments. Those skilled in the art will recognize that variations and modifications can be made without departing from the spirit of the invention. For example, additional layers can be added to provide thermal insulation and corrosion protection. It is therefore intended to include within the invention all such variations and modifications as fall within the scope of the appended claims and equivalents thereof.

We claim:

1. A calorimetric hydrocarbon gas sensor comprising:
   an electrochemical oxygen pump including an internal electrode and an external electrode;
   a sensing element including a catalyst and an interface region overlying the catalyst;
   a substrate having a plurality of overlying insulative layers, the substrate positioned intermediate to the electrochemical oxygen pump and the sensing element,
   wherein at least one of the plurality of overlying insulative layers includes a primary heater for regulating the temperature of the electrochemical oxygen pump, and
   wherein at least one the plurality of overlying insulative layers includes a temperature compensation heater for regulating the temperature of the catalyst, and
   wherein the electrochemical oxygen pump, the substrate, and the sensing element are vertically aligned in a stacked relationship and located in a substantially isothermal temperature zone.

2. The calorimetric hydrocarbon gas sensor of claim 1, wherein the primary heater regulates the temperature of the substrate to a first temperature, and wherein the temperature compensation heater compensates for heat produced by the catalyst and maintains its temperature at the first temperature.

3. The calorimetric hydrocarbon gas sensor of claim 1, further comprising at least one via in the substrate extending from a region proximate the internal electrode to the interface region.

4. The calorimetric hydrocarbon gas sensor of claim 3, wherein the catalyst comprises a reference region and an active region and wherein the at least one via is located proximate to the reference region and to the active region.

5. The calorimetric hydrocarbon gas sensor of claim 1, wherein the interface region comprises a gas transport layer overlying the catalyst.

6. A calorimetric hydrocarbon gas sensor comprising:
   an electrochemical oxygen pump;
   a sensing element including a catalyst;
   a multi-layer substrate positioned intermediate to the electrochemical oxygen pump and the sensing element, the multi-layer substrate including a plurality of overlying layers,
   wherein at least one of the plurality of overlying layers supports a temperature compensation heater positioned in proximity to the catalyst, and
   wherein at least one other of the plurality of overlying layers supports a primary heater in proximity to the electrochemical oxygen pump;
   temperature control circuitry configured to generate a control signal for controlling heat output of the primary heater; and
   calibration circuitry for providing a temperature calibration signal, such that the temperature calibration signal is transmitted at a different frequency than the control signal.

7. The calorimetric hydrocarbon gas sensor of claim 6 further comprising a thermometer positioned intermediate to the catalyst and the compensation heater.

8. The calorimetric hydrocarbon gas sensor of claim 6, further comprising at least one via in the multi-layer substrate extending through the multi-layer substrate from a region proximate the electrochemical oxygen pump to the sensing element.

9. The calorimetric hydrocarbon gas sensor of claim 6, wherein the electrochemical oxygen pump, the multi-layer substrate, and the sensing element are vertically aligned in a stacked relationship.

10. A calorimetric hydrocarbon gas sensor comprising:
    a reference catalyst adjacent to an active catalyst;
    a reference thermometer and a reference compensation heater in spaced relationship with the reference catalyst;
    an active thermometer and an active compensation heater in spaced relationship with the active catalyst;
    a primary heater configured to supply heat to the reference thermometer and to the active thermometer;
    control circuitry coupled to the reference thermometer, the active thermometer, reference and active compensation heaters, and the primary heater,
    wherein the control circuitry maintains a constant temperature difference between the reference thermometer and the active thermometer,
    wherein the control circuitry measures a difference in heat generated between the reference catalyst and the active catalyst,
    and wherein the control circuitry includes,
       temperature control circuitry configured to generate a control signal for controlling heat output of the primary heater, and
       calibration circuitry for providing a temperature calibration signal, such that the temperature calibration signal is transmitted at a different frequency than the control signal.

11. The calorimetric hydrocarbon gas sensor of claim 10, wherein the control circuitry further includes:
    reference thermometer control circuitry coupled to the reference thermometer and to the primary heater,
    including a reference thermometer voltage measurement circuit and a reference current source circuit and a voltage controller configured to receive a reference voltage signal from the reference thermometer and to receive a nominal operating voltage and to output a control signal to the primary heater equal to the difference between the reference voltage signal and the nominal operating voltage.

12. The calorimetric hydrocarbon gas sensor of claim 11, wherein the control circuitry further includes:
    reference compensation heater control circuitry coupled to the reference compensation heater,
    including a voltage summation circuit configured to receive a compensation voltage signal and a nominal gain signal and to output a voltage signal to the reference compensation heater, and power measurement circuit configured to receive a current signal from the reference compensation heater and the voltage signal from the voltage summation circuit.

13. The calorimetric hydrocarbon gas sensor of claim 12, wherein the control circuitry further includes:
    active compensation heater control circuitry coupled to the active compensation heater,
    including a voltage summation circuit configured to receive a compensation voltage signal and a computed gain signal and to output a voltage signal to the active compensation heater, and power measurement circuit configured to receive a current signal from the active compensation heater and the voltage signal from the voltage summation circuit.

14. A calorimetric hydrocarbon gas sensor comprising:
    a reference catalyst adjacent to an active catalyst;
    a reference thermometer and a reference compensation heater in spaced relationship with the reference catalyst;
    an active thermometer and an active compensation heater in spaced relationship with the active catalyst;
    a primary heater configured to supply heat to the reference thermometer and to the active thermometer; and
    control circuitry coupled to the reference thermometer, the active thermometer, reference and active compensation heaters, and the primary heater,
    wherein the control circuitry maintains a constant temperature difference between reference thermometer and the active thermometer,
    wherein the control circuitry measures a difference in heat generated between the reference catalyst and the active catalyst, and
    wherein the control circuitry includes,
       temperature control circuitry configured to generate a control signal for controlling heat output of the primary heater;
       temperature compensation circuitry for providing electrical control of the active and reference compensation heaters;
       power measurement circuitry for measuring differential power supplied to the active and reference compensation heaters; and
       calibration circuitry for providing a temperature calibration signal, such that the temperature calibration signal is transmitted at a different frequency than the control signal.

* * * * *